United States Patent
Eddy et al.

(10) Patent No.: US 9,968,911 B2
(45) Date of Patent: May 15, 2018

(54) BIOCHAR PRODUCTS AND METHOD OF MANUFACTURE THEREOF

(71) Applicant: The Carbon Basis Company Ltd., Beaumont (CA)

(72) Inventors: Leonard Bruce Eddy, Beaumont (CA); Paul Byron Tiege, Red Deer County (CA); Hilke Beuck, Sundre (CA); Greg Rekken, Calgary (CA)

(*) Notice: Subject to any disclaimer, the term of this patent is extended or adjusted under 35 U.S.C. 154(b) by 153 days.

(21) Appl. No.: 14/878,293

(22) Filed: Oct. 8, 2015

(65) Prior Publication Data

US 2016/0030922 A1    Feb. 4, 2016

Related U.S. Application Data

(60) Continuation-in-part of application No. 14/621,839, filed on Feb. 13, 2015, now abandoned, which is a
(Continued)

(51) Int. Cl.
*B01J 20/282*    (2006.01)
*B01J 20/30*     (2006.01)
(Continued)

(52) U.S. Cl.
CPC ......... *B01J 20/3007* (2013.01); *A23K 20/105* (2016.05); *A23K 20/163* (2016.05); *A23K 20/20* (2016.05); *B01J 20/20* (2013.01); *B01J 20/24* (2013.01); *B01J 20/261* (2013.01); *B01J 20/2803* (2013.01); *B01J 20/28019* (2013.01);
(Continued)

(58) Field of Classification Search
None
See application file for complete search history.

(56) References Cited

U.S. PATENT DOCUMENTS

| 2,340,567 A | 2/1944 | Sargent et al. |
| 2,684,295 A | 7/1954 | Eyster |

(Continued)

FOREIGN PATENT DOCUMENTS

| BR | 8603983 | * | 4/1988 |
| CN | 1704382 A | | 12/2005 |

(Continued)

OTHER PUBLICATIONS

"[biochar] Biochar with clay", tech.groups.yahoo.com/group/biocharimessage/306, Yahoo Mail.
(Continued)

*Primary Examiner* — Wayne Langel
(74) *Attorney, Agent, or Firm* — Brion Raffoul

(57) ABSTRACT

A method for producing charcoal particles or pellets which use different additives as binders for the biochar pellets. The method includes producing a mixture with charcoal and additives selected from nanocrystalline cellulose, bentonite, and polyvinyl acetate. The mixture is created by mixing one or more of the additives with charcoal and water. The mixture is then processed in a pelletizer device. While processing, the surface of the mixture is sprayed with a liquid. Once turned into pellets by way of the pelletizer device, the resulting pellets are then dried by applying heat to the pellets. The liquid can be water or a solution of water and sodium borate.

9 Claims, 2 Drawing Sheets

Related U.S. Application Data division of application No. 13/951,050, filed on Jul. 25, 2013, now Pat. No. 8,986,581.

(60) Provisional application No. 61/676,399, filed on Jul. 27, 2012.

(51) Int. Cl.
*B09C 1/08* (2006.01)
*B01J 20/20* (2006.01)
*B01J 20/24* (2006.01)
*B01J 20/26* (2006.01)
*B01J 31/06* (2006.01)
*B01J 20/28* (2006.01)
*B01J 20/32* (2006.01)
*C05F 11/00* (2006.01)
*C05F 11/02* (2006.01)
*C05G 3/00* (2006.01)
*A23K 20/105* (2016.01)
*A23K 20/163* (2016.01)
*A23K 20/20* (2016.01)
*B01J 21/18* (2006.01)

(52) U.S. Cl.
CPC ..... *B01J 20/28042* (2013.01); *B01J 20/3028* (2013.01); *B01J 20/3042* (2013.01); *B01J 20/3078* (2013.01); *B01J 20/3204* (2013.01); *B01J 20/3234* (2013.01); *B01J 31/06* (2013.01); *C05F 11/00* (2013.01); *C05F 11/02* (2013.01); *C05G 3/00* (2013.01); *C05G 3/0058* (2013.01); *B01J 20/282* (2013.01); *B01J 21/18* (2013.01); *B01J 2220/485* (2013.01); *B01J 2220/4837* (2013.01); *B01J 2231/49* (2013.01); *B09C 1/08* (2013.01)

(56) References Cited

U.S. PATENT DOCUMENTS

| | | |
|---|---|---|
| 3,295,950 A | 1/1967 | Blouin et al. |
| 3,342,577 A | 9/1967 | Blouin et al. |
| 3,576,613 A | 4/1971 | Fleming |
| 3,837,835 A | 9/1974 | Weinrotter et al. |
| 3,903,333 A | 9/1975 | Shirley, Jr. et al. |
| 3,991,225 A | 11/1976 | Blouin |
| 4,015,972 A | 4/1977 | Watkins et al. |
| 4,032,319 A | 6/1977 | Smith et al. |
| 4,042,366 A | 8/1977 | Fersch et al. |
| 4,081,264 A | 3/1978 | Ali |
| 4,133,668 A | 1/1979 | Young |
| 4,142,885 A | 3/1979 | Heumann et al. |
| 4,168,919 A | 9/1979 | Rosen et al. |
| 4,219,347 A | 8/1980 | Young |
| 4,302,237 A | 11/1981 | Young |
| 4,325,849 A | 4/1982 | Rosen et al. |
| 4,326,875 A | 4/1982 | Young |
| 4,460,612 A | 7/1984 | Saleeb et al. |
| 4,493,725 A | 1/1985 | Moon et al. |
| 4,587,358 A | 5/1986 | Blouin |
| 4,636,242 A | 1/1987 | Timmons |
| 4,664,683 A * | 5/1987 | Degen ................ A62B 19/00 210/502.1 |
| 4,676,821 A | 6/1987 | Gullett et al. |
| 4,762,546 A | 8/1988 | Boles |
| 4,842,790 A | 6/1989 | Nunnelly |
| 4,846,844 A | 7/1989 | De Leon et al. |
| 4,846,871 A | 7/1989 | Detroit |
| 4,847,087 A | 7/1989 | Young |
| 4,857,098 A | 8/1989 | Shirley, Jr. et al. |
| 4,857,243 A | 8/1989 | Von Blücher Hubert et al. |
| 4,952,419 A | 8/1990 | De Leon et al. |
| 4,954,134 A | 9/1990 | Harrison |
| 5,032,164 A | 7/1991 | Sanford et al. |
| 5,041,153 A | 8/1991 | Detroit |
| 5,043,007 A | 8/1991 | Davis |
| 5,112,379 A | 5/1992 | Young |
| H1085 H | 8/1992 | Simmons et al. |
| 5,169,647 A | 12/1992 | Young |
| 5,174,804 A | 12/1992 | Rehberg et al. |
| 5,211,985 A | 5/1993 | Shirley, Jr. et al. |
| 5,219,465 A | 6/1993 | Goertz et al. |
| 5,238,480 A | 8/1993 | Rehberg et al. |
| 5,240,490 A | 8/1993 | Moore et al. |
| 5,300,135 A | 4/1994 | Hudson et al. |
| 5,352,265 A | 10/1994 | Weston et al. |
| 5,399,186 A | 3/1995 | Derrah et al. |
| 5,407,442 A | 4/1995 | Karapasha |
| 5,454,851 A | 10/1995 | Zlotnikov et al. |
| 5,466,274 A | 11/1995 | Hudson et al. |
| 5,476,528 A | 12/1995 | Trimm et al. |
| 5,560,768 A | 10/1996 | Gordonov et al. |
| 5,599,374 A | 2/1997 | Detrick |
| 5,628,813 A | 5/1997 | Chen et al. |
| 5,676,727 A | 10/1997 | Radlein et al. |
| 5,788,896 A | 8/1998 | Bertram et al. |
| 5,944,960 A | 8/1999 | Nakata et al. |
| 6,287,496 B1 | 9/2001 | Lownds |
| 6,293,985 B1 | 9/2001 | Phinney |
| 6,331,193 B1 | 12/2001 | Phinney |
| 6,338,746 B1 | 1/2002 | Detrick et al. |
| 6,355,083 B1 | 3/2002 | Ogzewalla |
| 6,454,979 B1 | 9/2002 | Phinney |
| 6,500,223 B1 | 12/2002 | Sakai et al. |
| 6,503,287 B1 | 1/2003 | Schraven et al. |
| 6,509,440 B1 | 1/2003 | Sakane et al. |
| 6,558,445 B2 | 5/2003 | Hunter |
| 6,582,637 B1 | 6/2003 | Phinney |
| 6,787,234 B2 | 9/2004 | Tijsma et al. |
| 6,818,579 B2 | 11/2004 | Giangrasso |
| 6,864,351 B2 | 3/2005 | Sakane et al. |
| 7,189,275 B2 | 5/2007 | Pildysh |
| 7,220,469 B2 | 5/2007 | Sakane et al. |
| 7,371,444 B2 | 5/2008 | Kajikawa |
| 7,494,525 B2 | 2/2009 | Hojjatie et al. |
| 7,530,196 B2 | 5/2009 | Tidow et al. |
| 7,615,093 B2 | 11/2009 | Pildysh |
| 7,771,505 B2 | 8/2010 | Ogle et al. |
| 7,947,155 B1 | 5/2011 | Green et al. |
| 8,012,533 B2 | 9/2011 | Smith et al. |
| 8,361,186 B1 | 1/2013 | Shearer et al. |
| 8,709,122 B2 | 4/2014 | Lee et al. |
| 2004/0111968 A1 | 6/2004 | Day et al. |
| 2007/0029246 A1* | 2/2007 | Ueda ................ B01J 20/20 210/263 |
| 2007/0169527 A1 | 7/2007 | Wynnyk et al. |
| 2008/0040975 A1 | 2/2008 | Calderon |
| 2009/0126433 A1 | 5/2009 | Piskorz et al. |
| 2010/0162780 A1 | 7/2010 | Scharf |
| 2010/0312008 A1 | 12/2010 | Kastner et al. |
| 2012/0060574 A1* | 3/2012 | Rose ................ A01C 1/04 71/23 |
| 2012/0119398 A1* | 5/2012 | Mao ................ B01D 67/0067 264/29.1 |
| 2012/0125064 A1 | 5/2012 | Joseph et al. |
| 2012/0272702 A1 | 11/2012 | Martinez Rafael et al. |
| 2013/0031943 A1 | 2/2013 | Ferguson et al. |
| 2014/0290319 A1* | 10/2014 | Poo Palam ............ C05F 11/00 71/23 |
| 2015/0175492 A1 | 6/2015 | Allais et al. |
| 2015/0291480 A1* | 10/2015 | Nakajima ............ A01G 9/1086 71/23 |

FOREIGN PATENT DOCUMENTS

| | | |
|---|---|---|
| CN | 102659474 A | 9/2012 |
| CN | 102701833 A | 10/2012 |
| GB | 1171255 A | 11/1969 |
| GB | 1397355 A | 6/1975 |
| JP | 61138512 A | 6/1986 |
| JP | 08245280 A | 9/1996 |
| JP | 2002069428 | * 3/2002 |

(56) References Cited

FOREIGN PATENT DOCUMENTS

| | | | |
|---|---|---|---|
| JP | 2002159224 | * | 6/2002 |
| JP | 2004339042 A | | 12/2004 |
| JP | 2007191748 | * | 8/2007 |
| KR | 20030013491 A | | 2/2003 |
| KR | 2013067004 | * | 6/2013 |
| WO | 8911462 A1 | | 11/1989 |
| WO | 9429239 A1 | | 12/1994 |
| WO | 2010129988 A1 | | 11/2010 |

OTHER PUBLICATIONS

Dehkhoda, "Developing Biochar-Based Catalyst for Biodiesel Production", University of British Columbia, Aug. 2010.
"Effects of mycorrhizal fungi and biochar 75 days", www.energeticforum.com/agriculture/1647-effects-mycorrhizalfungi-biochar-5-days.html.
Keith, Lawrence H., "Final Report: Commercialization of Solid Acid and Base Catalysts Derived from Biochar Optimized to Produce Biodiesel from Low Cost Oils", cfpub.epa.gov/ncer_abstracts/index.cfm/fuseaction/display.abstractDetail/abstract19125/report/F, USEPA.
Garcia-Perez, Manuel et al., "Methods for Producing Biochar and Advanced Bio-fuels in Washington State, Part 3: Literature Review, Technologies for Product Collection and Refining", Department of Ecology State of Washington, Washington State University.
"Agrichar Biochar as a Soil Amendment", (2010) Pacific Pyrolysis, The Australian and New Zealand Biochar Researchers Network, Pacific Pyrolysis Pty Ltd.
Sumiball Ltd, "Sumi Ball", www.sumiball.com.
"Tiger 90CR Sulphur", www.tigersul.com/products/agriculture/bentonite-sulphor/tiger-90-cr-sulphur.html, TIGER-SUL.
Yu, Joyleen T. et al., "Development of Biochar-based Catalyst for Transesterification of Canola Oil", Energy Fuels 2011, 25, pp. 337-344.
Dehkhoda et al., "Biochar Based Solid Acid Catalyst for Biodiesal Production", Applied Catalysis, 2010, vol. 382, pp. 197-204.
Hill et al., "Effect of Sulphur Levels in Urea-Treated Corn Silage Diets [Cattle Diets]", Sulphur-in-agriculture (USA). 1984. v. 8 p. 8-10.
Kastner et al., "Catalytic Esterification of Fatty Acids Using Solid Acid Catalysts Generated from Biochar and Activated Carbon", Catalysis Today, 2012, vol. 190, issue 1, pp. 122-132.
Kutlu et al., "Effects of Providing Dietary Wood (Oak) Charcoal to Broiler Chicks and Laying Hens", Animal Feed Science and Technology, vol. 90, issues 3-4, Apr. 16 2001, pp. 213-226.
Morrison, M. et al., "Nutrient Metabolism and Rumen Micro-Organisms in Sheep Fed a Poor-Quality Tropical Grass Hay Supplemented With Sulphate", The Journal of Agriculture Science, vol. 115, issue 2, Oct. 1990, pp. 269-275.
Tisdale, Samuel L., "Sulphur in Forage Quality and Ruminant Nutrition", Washington: Sulphur Institute, 1977, v 13.
Mundt et al., "Control of Coccidiosis due to Eimeria bovis and Eimeria zuernii in Calves with Toltrazuril under Field Conditions in Comparison with Diclazuril and Untreated Controls", Parasitol Resistance (2007), 101 (Supplement 1): 93-104, 17661113, Cit:2.
Naka et al., "Adsorption Effect of Activated Charcoal on Enterohemorrhagic *Escherichia coli*", Nov. 2000.
Watarai et al., "Feeding Activated Charcoal from Bark Containing Wood Vinegar Liquid (Nekka-Rich) Is Effective as Treatment for Cryptosporidiosis in Calves", American Dairy Science Association, 2008, Journal of Dairy Science vol. 91 No. 4, 2008, pp. 1458-1463.
Dumroese et al., "Pelleted biochar: Chemical and physical properties show potential use as a substrate in container nurseries", www.elsevier.com/locate/niombioe, Biomass and Bioenergy 35 (2011) 2018-2027.
"Methods for Producing Biochar and Advanced Biofuels in Washington State", https://fortress.wa.gov/ecy/publications/publications/1107017.pdf.
Angelova, L., Terech, P., Natali, I., Dei, L., Carretti, E., & Weiss, R. (2011). Cosolvent Gel-like Materials from Partially Hydrolyzed Poly(vinyl acetate)s and Borax. Langmuir, 11671-11682.
Habibi, Y., Lucia, L., & Rojas, O. (2010). Cellulose Nanocrystals: Chemistry, Self-Assembly, and Applications. Chemical Reviews Chem. Rev., 3479-3500.
Kaboorani, A., Riedl, B., Blanchet, P., Fellin, M., Hosseinaei, O., & Wang, S. (n.d.). Nanocrystalline cellulose (NCC): A renewable nano-material for polyvinyl acetate (PVA) adhesive. European Polymer Journal, 1829-1837.
Lam, E., Male, K., Chong, J., Leung, A., & Luang, J. (n.d.). Applications of functionalized and nanoparticle-modified nanocrystalline cellulose. Trends in Biotechnology, 283-290.
Moon, R., Martini, A., Nairn, J., Simonsen, J., & Youngblood, J. (n.d.). Cellulose nanomaterials review: Structure, properties and nanocornposites. Chemical Society Reviews Chem. Soc. Rev., 3941-3941.
Peng, B., Dhar, N., Liu, H., & Tam, K. (2011). Chemistry and applications of nanocrystalline cellulose and its derivatives: A nanotechnology perspective. Can. J. Chem. Eng. The Canadian Journal of Chemical Engineering, 1191-1206.
Siqueira, G., Bras, J., & Dufresne, A. (n.d.). Cellulosic Bionanocomposites: A Review of Preparation, Properties and Applications. Polymers, 728-765.
Tetreau, J. P. (2010). Impact of Nanotechnology in Alberta.
What are CelluloseNanoCrystals? (2013). Retrieved Nov. 24, 2015, from https://www.youtube.com/watch?v=ktJXVeaQIBI.

* cited by examiner

BIOCHAR PRODUCTS AND METHOD OF MANUFACTURE THEREOF

RELATED APPLICATIONS

This application is a Continuation-in-Part of U.S. patent application Ser. No. 14/621,839 filed Feb. 13, 2015, which is a Divisional of U.S. patent application Ser. No. 13/951,050 filed Jul. 25, 2013, which claims benefit of U.S. Provisional Application No. 61/676,399 filed Jul. 27, 2012.

TECHNICAL FIELD

The present invention relates to a biochar or charcoal product and methods of producing the biochar product which incorporates different additives.

BACKGROUND OF THE INVENTION

Biochar is a highly porous carbonized material that can be found on the soil after a forest has burned. The porous nature of biochar and other charcoal products has been found to provide a habitat for beneficial microbes that absorb toxins in the soil and convert organic detritus into useful materials for the growth of nascent plants.

Synthetic charcoal products and biochar can be made on an industrial scale by burning wood chips and other cellulosic materials in an oxygen deficient atmosphere. Biochar in particular has a remedial benefit on the soil due mainly to the highly porous nature of the charcoal it contains. These pores are able to absorb toxic metals and accommodate beneficial microbes that feed on the remaining organics, leaving the soil fit for plant growth.

Synthetic biochar is made and traded worldwide. It is used mainly for soil remediation and improved plant growth. Early manufacturing processes were essentially based upon those for making pure charcoal. The feedstock can be any cellulose containing material that will breakdown under anoxic conditions to produce charcoal. Wood chips are preferred. Although the cellulose in the wood decomposes mainly to carbon and water, at high temperatures, a side reaction converts some charcoal into biogases and bioliquids. As biochar is not a pure charcoal, it is sold at a lower price. The reaction by-products reduce the value further, as they are only marketable as cheap fuel.

The particles of synthetic biochar may be distributed on the soil with equipment used for other agricultural products, such as plant seed and pelletized fertilizer. However, since the charcoal in the biochar is somewhat friable, distribution using conventional agriculture equipment creates hazardous dust, and loss of useful product. Furthermore, the low bulk density and lack of particle sizing control of the biochar causes separation of any blend of biochar and plant seed and/or commercial fertilizer during handling and distribution. To overcome this problem, methods have been developed to protect the biochar particles with a layer of an inert ceramic material. This approach has been found to minimize product breakdown and increase bulk density. As the ceramic coating needs to be sintered at high temperature, undesirable by-products are formed at the expense of some of the charcoal. Also, the inert coating simply disintegrates into small particles that remain in the soil.

It should be noted that biochar may also be used in other industries. Biodiesel for sale as transportation fuel in Canada and the United States must meet strict quality guidelines (CAN/CGSB-3.524-2011 in Canada and ASTM 6751 in the U.S.). Biodiesel must have low water and glycerol content. Often biodiesel manufacturers must use post-manufacturing desiccants and absorptive resins to remove unwanted contaminants before the quality of the biodiesel is sufficient for sale. This is sometimes referred to as "polishing." A biochar-based polishing agent would be advantageous because it is environmentally benign unlike some polymeric polishing agents. Thus, disposal of the bio-based based agent after polishing may be seen as having less of a negative impact. Because biochar is dusty and comprised of small particles that would contaminate the biodiesel, using un-pelleted biochar is not an option to absorb unwanted liquid contaminants such as water from transportation fuel. However, if biochar is densified into pellets that are robust and non-dusty, the product can be used as a polishing agent without introducing further contamination.

A biochar product that can be used as noted above would therefore be advantageous. Not only that, but a process for producing such a product, with mechanical properties that allow its use in the biodiesel industry, would also be advantageous and desirable.

SUMMARY OF INVENTION

The present invention provides a method for producing biochar particles or pellets which use different additives as binders for the biochar pellets. The method includes producing a mixture with biochar and additives selected from bentonite clay, nanocrystalline cellulose, and polyvinyl acetate. The mixture is created by mixing one or more of the additives with charcoal and water. The mixture is then processed in a pelletizer device. While processing, the surface of the mixture is sprayed with a liquid. Once turned into pellets by way of the pelletizer device, the resulting pellets are then dried by applying heat to the pellets. The liquid can be water or a solution of water and sodium borate.

In a first aspect, the present invention provides a charcoal product comprising a porous charcoal pellet having additives selected from a group comprising bentonite clay, nanocrystalline cellulose, polyvinyl acetate, and sodium borate.

In a second aspect, the present invention provides a method for producing charcoal pellets, the method comprising:
 a) mixing charcoal with at least one additive and water to result in a mixture;
 b) processing said mixture in a pelletizer device which forces said mixture to tumble and to form pellets;
 c) spraying said mixture with a liquid while said mixture is being processed in said pelletizer device; and
 d) heating pellets resulting from steps b) and c) to dry said pellets.

In another aspect, the present invention provides a charcoal product comprising a porous charcoal pellet manufactured from charcoal, bentonite, and water and at least one additive selected from a group consisting of: nanocrystalline cellulose, polyvinyl acetate, and sodium borate.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
FIG. 1 is a photograph of the resulting charcoal pellets using PVA as a binder.

The present invention, in one embodiment, provides a biochar or charcoal product having a binding agent which may be bentonite, nanocrystalline cellulose, or polyvinyl acetate. The binding agents and the methods disclosed are low-energy and inexpensive routes for obtaining a desirable product and do not require specialized equipment.

It should be clear that the term "biochar" as used in this document means charcoal sourced from cellulose-based feedstock and is for use in improving soils. However, for the purposes of the present invention, the terms biochar and charcoal are used interchangeably and the term "biochar" should not be taken to limit the scope of the invention.

To obtain the charcoal for use in the production of the biochar or charcoal products of the invention, it is preferred to use charcoal with a uniform sizing of charcoal particles. Unactivated charcoal made from pine wood chips was purchased and presented with a wide variety of particles sizes and moisture content percentages. Charcoal preparation is critical to efficient pelleting regardless of the additives or methodology, and it was found that a uniform distribution of charcoal particles between 40 and 180 micron performed the best, which required a drying, sizing and sorting preparation process. A Unotec™ silage mixer with three horizontal mixing augers was modified to have three 2" collars welded to the bottom where heated air was forced through a manifold using a 1.5 hp Keho™ blower. This system enabled up to 6 yards of charcoal to be mixed and dried over the course of 2-3 days of continuous operation.

The dried charcoal was then fed into a Buskirk Engineering HM1000™ hammer mill for particle reduction; charcoal that was too wet plugged the system, while insufficient processing occurred if the charcoal was too dry. It was found that drying process must be tightly controlled to ensure that the charcoal moisture content (percent based on weight) was between 5% and 11%. A Sweco LS 24™ separator was used for size sorting in combination with an Oneida™ 2 hp cyclone creating a negative pressure throughout the system. The undersized particles can be incorporated with the pelleting mix to avoid waste, whereas the oversized particles must be recycled through the hammer mill.

A pelletizer device is used for mixing biochar or charcoal with an appropriate additive which acts as a binding or adhesion agent. The mixture is then aggregated in a rotating pelletizer device. In one implementation, the pelletizer device is a rotating drum with an adjustable drum angle. The bottom of the drum has a rough textured surface that pulls the mixture up and around. As the mixture is tumbled repeatedly through the drum, the mixture starts to stick together in small particles which then glomerate or aggregate into larger and rounder pellets. The drum angle can be set to different angles from horizontal. The Agglo-Miser™ device manufactured by Mars Minerals was used in one implementation.

According to one aspect of the invention, NCC (nanocrystalline cellulose) can be used as one of the binders for the biochar pellets. NCC is pure cellulose in crystalline form that is rod shaped, 1-100 nm in diameter and 10-200 nm in length and characterized as one of the strongest and stiffest natural materials available. NCC is biodegradable and non-toxic with unique properties in suspension such as self-assembly that make it a suitable candidate for biocomposites and binders. NCC has been found to improve the strength of some glues, including polyvinyl acetate (PVA) used in engineering wood products. This is thought to be a consequence of NCC dispersion and self-assembly in a PVA suspension. The outcome of these trials whereby NCC was added to charcoal and bentonite clay mixture illustrate how it may improve the adsorbtion qualities of the final product to yield a dense, durable high quality pellet. An optimal mixture using a PVA/NCC could be blended with a host of other additives to produce low-cost pellets that are durable enough to be handled using industrial equipment and to resist deterioration under a number of different applications, including liquids filtration.

It should be noted, for clarity, that nanocrystalline cellulose is produced after acid hydrolysis of market pulp as a source of cellulose and then refined during a centrifuge/filtration process.

In one implementation of the present invention, cat litter was used as a source of bentonite clay. This impure bentonite is a mix of mostly calcium bentonite, some sodium bentonite and other contaminants. To use the cat litter for this invention, the cat litter was ground and sieved to a maximum size of 1 mm to remove any large contaminating foreign matter such as pebbles.

It should be noted that, for the purposes of this invention, the term "bentonite" and "bentonite clay" is to include sodium bentonite, sodium bentonite, other types of bentonite, and any mixtures thereof.

When charcoal is to be used with bentonite, ground charcoal is mixed with a desired amount of bentonite and enough water to eliminate dust, but not to become noticeably wet. Pre-wetting reduced charcoal dust and improved pelleting performance. The pre-wetted mixture is then sieved to 2 mm prior to pelleting resulted in more consistent and manageable pellet size.

It should be noted that slowly adding water as a fine mist through a paint sprayer during pelleting was found to be another useful step in ensuring consistent formation of small pellets. Many short applications of water (at a pressure of approximately 0.5 bar] were performed every few minutes. The water was directed at the surface of the tumbling mixture in the pelletizer. To avoid over-wetting, the water was allowed to thoroughly mix for a few minutes between applications.

As will be seen in the examples below, a number of different mixture ratios of bentonite and charcoal were tried. However, the best results were produced using a 2:1 ratio between bentonite and charcoal.

Bentonite clay is a preferred binder for biochar as:
It is cheap and widely available in U.S.A. and Canada.
  Bentonite is commonly used in drilling muds.
Bentonite is a completely natural product.
Charcoal pellets made with bentonite binder, depending on the absorbate, could be composted or applied to land after use.
In addition to being an inert vehicle for carrying nutrients, fertilizers, etc., charcoal/bentonite pellets can be used for a range of applications including animal feed supplements, horticultural growing media, solid acid catalysts, desiccants and polishing agents, and for soil improvement and reclamation.

Another useful additive and/or binder for biochar/charcoal pellets is polyvinyl acetate (PVA) and sodium borate (borax). The charcoal pellets can be bound using a mixture of poly(vinyl acetate) (PVA) and sodium borate (borax). Borate is known to cross-link PVA to form gels. These aqueous mixtures harden upon loss of water. It has been found that incorporating charcoal into cross-linked PVA/ borax mixtures allows for the formation of a cohesive particle. This cohesive particle was found to be amenable to forming a generally spherical particle on random tumbling and this particle then hardens to a hard, dustless pellet upon drying. It was found that the PVA/borax mixture need not be formed prior to introduction of charcoal. Indeed, from a practical perspective, it is more advantageous to mix charcoal into PVA solutions first, then, by introduction of borax solution to the surface of such mixture, form the desired pellets.

For the examples provided, the PVA solutions used were commercial white glue. For example, the commercial white glue used was 37.5% PVA, 62.5% water by mass. By incorporating charcoal into PVA solutions, handling of the charcoal is greatly improved and dust levels are controlled. A photograph of charcoal pellets which used PVA as a binder is provided in FIG. 1.

The biochar/charcoal pellets of the present invention can be manufactured using the various methods disclosed below.

Figure 2:
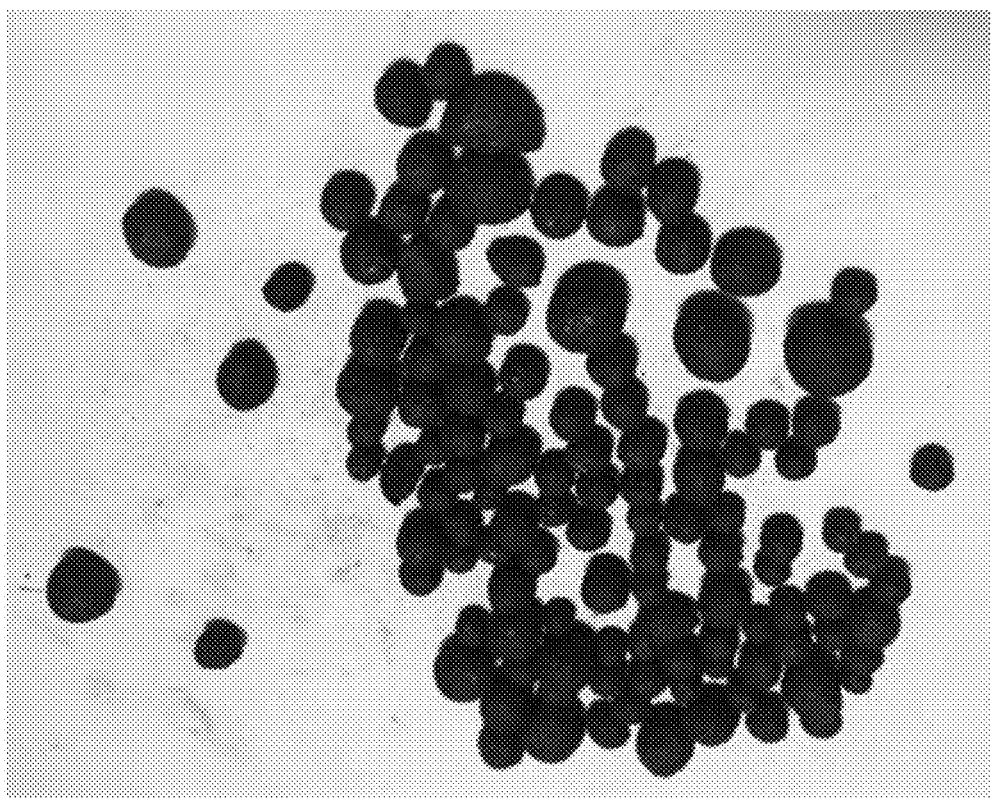
FIG. 2 is a photograph of the resulting charcoal pellets using bentonite clay as a binder.

In one method, bentonite clay is used as a binder and water is used as a texture modifier for the biochar/charcoal. In one example only bentonite clay, charcoal and water are used in the pelleting mixture. In a variant, only bentonite clay, charcoal, nanocrystalline cellulose and water are used for the pelleting mixture. The pelleting is performed using a rotating pelletizer at room temperature (approx. 20° C.) The rotating drum of the pelletizer is set between 10° and 40°, preferably at 15-25°. The pre-moistened bentonite and charcoal mixture is loaded into the pelletizer and the pelletizer is allowed to rotate with the angle set such that pelleted material, of different bulk density than unpelleted material, migrates to the front of the pan to leave a substantially enriched zone of pelleted material and a substantially enriched zone of unpelleted material. The discharge mechanism can be set so that material is removed from the pelletizer as new, unpelleted material is introduced. This allows for the operation in a semi-batch mode, or the operation may occur in batch mode. In semi-batch mode, the pelleting matter is kept in the pelletizer such that material exits the pelletizer in substantially "finished" pellet form. FIG. 2 is a photograph of the resulting charcoal pellets which used bentonite as a binder.

It should be noted that water is preferably added to the mixture in the pelletizer. In either batch or semi-batch operation, water is slowly introduced to the surface of the mixture as it is mixing using a fine mist sprayer at low volume and low pressure, thereby maintaining a mixing moisture level adequate to sustain pelleting. Applied water is allowed to homogenize or mix between applications. Excessive moisture or excessively fast addition of water can cause clumping and larger aggregate growth. Conversely, inadequate moisture results in no pellet formation. Further, if the pellets are left too long in the pelletizer, smaller pellets aggregate into large, non-uniform pellets. Once the pellets are formed, the resulting pellets can then be dried in an oven.

In another aspect of the invention, instead of bentonite clay, polyvinyl acetate (PVA) is used as a binder. For this variant of the invention, PVA and water are mixed with charcoal to form a paste. The paste is then sieved and then placed in a rotating pelletizer. As the paste is pelletized, a mixture of water and sodium borate (borax) is sprayed on to the paste. The resulting pellets are then dried in an oven for approximately 24 hours.

The following are examples of implementations of the variants of the present invention. The following examples should be taken as illustrative and not an exhaustive or as limiting to the scope of the present invention.

Example 1

300 g of bentonite clay and 150 g of pre-prepared charcoal are mixed and then loaded into a rotating pelletizer drum. The mixture is misted with water from a low-pressure atomizer (e.g. an automobile paint gun). A total of 275 mL of water is applied. The mixture is mixed in the rotating drum set at an elevation of 20° for 2 hours at room temperature (approximately 18-21° C.), after which time the mixture consists mainly of pellets of 1 mm-1 cm diameter. The pellets are removed from the drum and dried at 70° C. for 24 hours. Pellet strength varied from weak to hard, dustless pellets.

Example 2

200 g of bentonite clay, 100 g of prepared charcoal and 50 g of nanocrystalline cellulose are premixed then loaded into a rotating pelletizer drum. The mixture is misted with water from a low-pressure atomizer (e.g. an automobile paint gun). A total of 275 mL water is applied. The mixture is mixed in the rotating drum set at 20° for 1 hour and ten minutes at room temperature, then dried at 70° C. for one hour. The mixture is then loaded back into the pelletizer for 40 minutes after which time the mixture consists mainly of pellets of 1 mm-1 cm diameter. The pellets are removed from the drum and dried at 70° C. Pellets are hard, angular and dustless, mainly 1-5 mm.

It should be noted that the nanocrystalline cellulose was mixed with finely ground, sieved bentonite clay by mixing in a bread dough mixer or by hand using a mortar and pestle. Once the nanocrystalline cellulose and the bentonite have been mixed, the resulting mixture was combined with the charcoal.

Example 3

400 g of bentonite and 200 g of prepared charcoal are pre-mixed then loaded into a rotating pelletizer drum. The mixture is misted with water from a low-pressure atomizer (e.g. an automobile paint gun). A total of 41 5 mL water is applied. The mixture is mixed in the rotating drum for one hour and ten minutes at room temperature, after which time the mixture consists mainly of pellets of 1 mm-4 mm diameter. The pellets are then removed from the pelletizer drum and dried at 70° C. to form dustless pellets of moderate strength.

Example 4

300 g of prepared charcoal was placed in a mixer and 200 mL water containing 15 g of commercial white glue (5.65 g of PVA) was mixed in to form a paste. The paste was sieved through a 2 mm sieve, then introduced into the rotating pelletizer. As the charcoal/PVA mixture mixed in the pelletizer, a solution of borax (15 g of sodium borate in a total of 500 mL of liquid) was applied to the surface of the mixture in short bursts using an automotive paint spray gun using an approximate pressure of 10 psi on the spray gun.

It should be noted that, when sodium borate is used, slow, careful addition of the borax solution is very useful for ensuring consistent pellet formation. For this example, four to six applications of the sodium borate solution were made with the applications being separated by a few minutes. Each application of the solution was directed to the surface of the mixture in the pelletizer. To avoid over-wetting, the charcoal was allowed to thoroughly mix for a few minutes between applications of the solution. The total amount of borax or sodium borate solution applied was 310 mL, using 9.3 g of sodium borate. The angle of the pelletizer was set at 25° for the first 5 minutes, then lowered to 18° for thirty minutes then finally decreased to 15° until the pellets formed. The pelleting temperature was approximately 20° C. After two hours, the pelleted product was removed from the pelletizer and dried in a gravity oven at 70° C. for 24 hours. The pellets were approximately 3-4 mm and not very spherical. Most of the resulting pellets were hard, but some were brittle.

Example 5

150 g of prepared charcoal was placed in a mixer and 200 mL water containing 20 g of commercial white glue (7.50 g of PVA) was mixed in to form a paste mixture. The paste mixture was sieved through a 2 mm sieve and then introduced into the rotating pelletizer. As the charcoal-PVA mixture mixed in the pelletizer, a solution of borax (10 g of sodium borate in 100 mL of water) was applied to the surface of the composition in short bursts by use of an automotive paint spray gun. The pressure setting for the spray guy was set to approximately 10 psi.

Similar to the procedure in Example 4 above, four to six applications of the borax solution were made every few minutes, each application being directed to the surface of the mixture. To avoid over-wetting, the charcoal was allowed to thoroughly mix for a few minutes between applications. The total amount of borax solution applied was 145 mL (containing a total of 14.5 g of sodium borate).

For the pelletizer, the angle of the pelletizer drum was set at 25° for the first 10 minutes, then lowered to 15° for sixteen minutes then finally decreased to 12° until the pellets formed. The pelleting temperature was approximately 20° C. After 2.5 hours in the pelletizer, the pelleted mixture was removed from the pelletizer and dried in a gravity oven at 70° C. for 24 hours. The pellets were fairly uniform in size at approximately 6-8 mm per pellet.

Example 6

300 g of prepared charcoal was placed in a mixer and 400 mL water containing 80 g of commercial white glue (with 30 g of PVA) was mixed in to form a paste mixture. The paste mixture was sieved through a 2 mm sieve and then introduced into the rotating pelletizer. As the charcoal-PVA mixture rotated in the pelletizer, a solution of borax (with a total of 50 g of sodium in 500 mL of water) was applied to the surface of the composition in short bursts using an automotive paint spray gun. The pressure setting for the spray gun was set at approximately 10 psi.

As with Examples 4 and 5 above, at total of four to six applications of the borax solution were made every few minutes, directed to the surface of the mixture. To avoid over-wetting, the charcoal was allowed to thoroughly mix for a few minutes between applications. The total amount of borax solution applied was 120 mL using 12 g of sodium borate.

For the pelletizer, the pelletizer drum was set at an angle of 25° for the first 5 minutes, then lowered to 18° for fifty minutes then finally decreased to 15° until the pellets formed. The pelleting temperature was approximately 20° C. After two hours, the resulting pellets were removed from the pelletizer and dried in a gravity oven at 70° C. for 24 hours. The pellets were fairly uniform in size, the majority being approximately 1-2 mm in size. Pellets were very hard and not dusty.

The resulting biochar/charcoal pellets were tested for their ability to absorb moisture from biodiesel. The results given below were obtained.

To demonstrate the utility of the charcoal pellets as absorbants, charcoal pellets were compared to commercial absorbants for their ability to absorb water from biodiesel. In one test, two samples of biodiesel were obtained and water was added to each to obtain a final water contents of 808.1 ppm (BDa) and 803.3 ppm (BDb) (measured by Karl Fischer titration). Two commercial absorbants, Eco2Pure™ and Purolite™ PD206 were tested against the charcoal pellets obtained using the procedure in Examples 3 and 6. The pellets from Example 3 used a bentonite binder while the pellets from Example 6 used a PVA/borax binder.

The commercial absorbants and the charcoal pellets were each loaded into glass chromatography columns equipped with Teflon stopcocks. 81.5 g of each test article was loaded into each of the chromatography columns and wet biodiesel was passed through each test article.

The residence time for the biodiesel (i.e. the time the biodiesel was in the columns) was adjusted beforehand so that the biodiesel contacted each sample for approximately the same amount of time. 100 mL of either BDa or BDb was passed through each test article and the water content of the biodiesel was measured after by Karl Fischer titration.

Oven-dried Eco2Pure reduced the water concentration by 92%, and Purolite (as-received) reduced the water concentration by 84%. Purolite, oven-dried to negligible moisture content reduced water concentration in biodiesel by 96%. The biochar pellets using bentonite as a binder reduced the water concentration by 81%. The biochar pellets using the PVA/borax mix as a binder reduced the water concentration in the biodiesel by 88%.

TABLE 1

Water concentration reduction in biodiesel by various absorbants

| Sample ID | Filtration time (h) | volume of pellets (mL) | weight of pellets (g) | Tested on | Water content (ppm) | water reduction in % |
|---|---|---|---|---|---|---|
| Wetted biodiesel batch 1 (BDa) | | | | | 808.1 ppm | |
| Wetted biodiesel batch 2 (BDb) | | | | | 803.3 ppm | |
| Eco2Pure | 2:16 | 330 | 81.5 | BDa | 65.6 ppm | 91.88% |
| Purolite | 1:55 | 100 | 81.5 | BDa | 128.6 ppm | 84.09% |
| Purolite(dried) | 1:58 | 100 | 81.5 | BDb | 34.7 ppm | 95.68% |
| Example 6 | 1:56 | 270 | 81.5 | BDb | 98.7 ppm | 87.71% |
| Example 3 | 1:59 | 143 | 81.5 | BDa | 154.5 ppm | 80.88% |

To further test the samples, a second test was run in which the volume, rather than the mass of the test absorbant, was kept constant. Approximately 46 mL of charcoal pellets obtained as discussed in Examples 1-5 were used. The samples were loaded into glass chromatography columns. A sample of biodiesel was obtained and wetted to a water concentration of 904.9 ppm (measured by Karl Fischer titration). Additional testing subjects (commercial absorbants from Eco2Pure™ and Purolite™) were each loaded into glass chromatography columns equipped with Teflon stopcocks and wet biodiesel was passed through each test article. As in the first test, the residence time was adjusted beforehand so that the biodiesel passed through each test article in approximately the same amount of time.

The charcoal pellets (using a charcoal:bentonite mass ratio of 1:2) from Example 3 (pelletized for 1 hours and ten minutes) only removed 15% of water. However, the charcoal pellets from Example 1 (using the same mass ratio of charcoal to bentonite but which was pelletized for 2 hours) removed 80% of water.

Most surprisingly, the charcoal pellets which used NCC in addition to the bentonite removed 90% of the water in the biodiesel. For this sample, a mass ratio of charcoal/bentonite/NCC of 2:24:1 was used. The charcoal/PVA/borax pellets obtained in Example 4 only removed 31% of the water while the charcoal/PVA/borax pellets from Example 5 removed 61% of water.

TABLE 2

Water concentration reduction of biodiesel by charcoal/bentonite and charcoal/PVA/borax pellets

| Sample ID | Filtration time (h) | volume of pellets (mL) | mass of pellets (g) | Water content | water reduction in % |
|---|---|---|---|---|---|
| Wetted biodiesel | | | | 904.9 ppm | |
| Example 5 | 1.24 | 45 | 11.49 | 349.1 ppm | 61.42% |
| Example 1 | 1.25 | 46 | 30.97 | 185.1 ppm | 79.54% |
| Example 2 | 1.25 | 47 | 27.85 | 85.7 ppm | 90.53% |
| Example 4 | 1.34 | 45 | 10.60 | 626.4 ppm | 30.78% |
| Example 3 | 1.15 | 46 | 25.22 | 772.8 ppm | 14.60% |

To demonstrate the utility of the charcoal pellets as glycerol absorbants, charcoal pellets were compared to commercial absorbants for their ability to absorb glycerol from crude biodiesel.

Two biodiesel samples were obtained with a glycerol content of 0.0034% and 0.0092% by mass (measured by gas chromatography). Two commercial absorbants, Eco2Pure™ and Purolite™ PD206, and the charcoal pellets obtained using the process in Example 6 and Example 3 were compared. The pellets from Example 6 used a PVA/borax binder while the pellets from Example 3 used a bentonite binder. The absorbants to be tested, along with the charcoal pellets, were each loaded separately into glass chromatography columns equipped with Teflon stopcocks. The test absorbants were loaded into each of the chromatography columns and biodiesel was passed through each test article. As with the tests above, the residence time was adjusted beforehand so that the biodiesel contacted each absorbant for approximately the same amount of time. 100 mL of biodiesel containing glycerol was passed through each test article and the glycerol content of the biodiesel was measured after this using gas chromatography. The Eco2Pure absorbant reduced the glycerol concentration by 41.7% while the Purolite absorbant reduced glycerol concentration by 91.3%. In comparison, the charcoal pellets which used the PVA/borax binder reduced the glycerol concentration by 26.5%. The charcoal pellets which used the bentonite binder reduced the glycerol content by 84.8%. The results are detailed in Table 3 below.

TABLE 3

Glycerol concentration reduction of biodiesel by charcoal/PVA/borax pellets compared to commercial absorbants

| Sample ID | Filtration time (h) | volume of pellets (mL) | mass of pellets (g) | Tested on | glycerol content (mass %) | glycerol reduction in % |
|---|---|---|---|---|---|---|
| Biodiesel with glycerol | | | | | 0.0034 | |
| Eco2Pure | 2:16 | 330 | 81.5 | BD#1 | 0.0020 | 41.2 |
| Purolite | 1:58 | 100 | 81.5 | BD#2 | 0.0008 | 91.3 |
| Example 6 | 1:56 | 270 | 81.5 | BD#1 | 0.0025 | 26.5 |
| Example 3 | 1:59 | 143 | 81.5 | BD#2 | 0.0014 | 84.8 |

As noted above, the resulting biochar pellets may be used in the manufacture of biodiesel. These biochar/charcoal pellets may also be used in esterifications and transesterification reactions other than biodiesel manufacture. The charcoal pellets may also be used as a convenient biodiesel desiccant. Alternatively, un-densified charcoal may also be used in a sealed cartridge or similar as a disposable fixed bed biodiesel desiccant. Accordingly, it should be clear that the resulting product may be used as a biodiesel desiccant, a transportation fuel desiccant, a dessicant for liquid hydrocarbon mixture, or as an organic solution desiccant.

The advantages of the resulting biochar/charcoal pellets are numerous. These charcoal pellets manufactured using the above procedures are inert to biodiesel at room temperature, i.e. they do not catalyze or react chemically with biodiesel. As another advantage, these biochar/charcoal pellets absorb unwanted biodiesel contaminants such as water and glycerol. The charcoal pellets also maintain their shape and do not dissolve (up to 48 hours tested), so the pellets are easily removed from the biodiesel. The shape and size of the pellets lends itself to convenient large-scale processing options, such as fixed-bed flow through reactors in which the charcoal desiccant remains stationary and the biodiesel is passed through the resin bed. The charcoal desiccant, when spent, can be disposed of harmlessly in landfills as a bio-based product.

The biochar/charcoal pellets may also be used for other purposes. As an example, the end product may be used as a supplement for animal feed. Activated charcoal is known to be effective at treating parasitic infections in different ruminant animals, including cattle and sheep (see Mundt, H-C., et al. Parasitol Resistance, August 2007; 101 (Supplement 1): 93-104, 17661113, Cit:2.). Therapeutic variants are sold commercially where charcoal is combined with various sulphaletamides for the treatment of coccidiosis infection in beef cattle, dairy cattle, veal and sheep. Research has shown that adding charcoal to the diet of chicken broilers and laying hens can improve growth performance during the first 28 days of fattening and reduced cracked eggs if added as a dietary supplement to laying hens (see Kutlu, H-R., Unsal, I., Gorgulu, M., Animal Feed Science and Technology, 2001, vol 90, n3-4, pp. 213-226. ISSN 0377-8401.).

For a more thorough understanding of the present invention, the following references may be consulted:

Edmond Lam, et al., Applications of functionalized and nanoparticle-modified nanocrystalline cellulose, Trends in Biotechnology, May 2012 Vol. 30, No. 5.

Habibi, Youssef, et al., Cellulose Nanocyrstals: Chemistry, Self-Assembly and Applications, March 2010, Chem. Rev. 110, pp. 3479-3500.

Tetreau,]P. Impact of Nanotechnology in Alberta, Nanocyrstalline Cellulose, Oct. 30, 2010, University of Alberta.

Kaboorani, A., et al., Nanocrystalline cellulose (NCC): A renewable nano-material for polyvinyl acetate (PVA) adhesive. European Polymer Journal 48, (2012) 1829-1837.

Habibi Y, Lucia L A, Rojas O J. (2010) Cellulose Nanocrystals: Chemistry, Self-assembly and Applications. Chemical Reviews 110:3479-3500

Peng B L, Dhar N, Liu H L, Tam K C. (2011) Chemistry and applications of nanocrystalline cellulose and its derivatives: A nanotechnology perspective. The Canadian Journal of Chemical Engineering 89[5]:1191-1206

Siqueira G, Bras J, Dufresne A. [2010] Polymers 2(4) 728-765

Moon R J, Martini A, Nairn J, Simonsen J, Youngblood J. (2011) Cellulose nanomaterials review: structure, properties and nanocomposites. Chem. Soc. Rev. 40:394-1-3994

Angelova L V, Terech P, Natali I, Dei L, Carretti E, Weiss R G. (2011) Cosolvent Gel-like Materials from Partially Hydrolyzed Poly(vinyl acetate)s and Borax. Langmuir 27:1 1671-1 1682

A person understanding this invention may now conceive of alternative structures and embodiments or variations of the above all of which are intended to fall within the scope of the invention as defined in the claims that follow.

We claim:

1. A charcoal product comprising a porous charcoal pellet having one or more additives selected from a group consisting of:
    nanocrystalline cellulose;
    nanocrystalline cellulose and water;
    polyvinyl acetate and sodium borate;
    bentonite, nanocrystalline cellulose, and water; and
    polyvinyl acetate, water and sodium borate.

2. A charcoal product according to claim 1, wherein said one or more additives comprises nanocrystalline cellulose and said product has a charcoal to nanocrystalline cellulose mass ratio of 2:1.

3. A charcoal product according to claim 1, wherein said polyvinyl acetate is used as a binder for said pellet.

4. A charcoal product according to claim 1, wherein said polyvinyl acetate and said sodium borate are used as binders for said pellet.

5. A charcoal product according to claim 1, wherein said product is for at least one of:
    biodiesel manufacturing;
    animal feed supplement;
    esterifications reactions;
    transesterification reactions;
    organic solution dessicant; and,
    liquid hydrocarbon mixture dessicant.

6. A charcoal product comprising a porous charcoal pellet manufactured from charcoal, bentonite, and water and at least one additive selected from a group consisting of: nanocrystalline cellulose, polyvinyl acetate, and sodium borate.

7. A charcoal product according to claim 6, wherein said product is for at least one of:
    biodiesel manufacturing;
    animal feed supplement;
    esterifications reactions;
    transesterification reactions;
    organic solution dessicant,
    liquid hydrocarbon mixture dessicant; and,
    liquids purification.

8. A charcoal product according to claim 6, wherein said at least one additive is nanocrystalline cellulose and said product has a charcoal to nanocrystalline cellulose mass ratio of 2:1.

9. A charcoal product according to claim 6, wherein said polyvinyl acetate and said sodium borate are used as binders for said pellet.

* * * * *